United States Patent
Zerbinati

(10) Patent No.: US 11,530,302 B2
(45) Date of Patent: Dec. 20, 2022

(54) METHOD TO PREPARE A FILLER WITH A HYALURONIC ACID BASE USING SPECIFIC CROSSLINKING AGENTS

(71) Applicant: MATEX LAB S.P.A., Brindisi (IT)

(72) Inventor: Nicola Zerbinati, Pavia (IT)

(73) Assignee: MATEX LAB S.P.A., Brindisi (IT)

( * ) Notice: Subject to any disclaimer, the term of this patent is extended or adjusted under 35 U.S.C. 154(b) by 0 days.

(21) Appl. No.: 16/959,141

(22) PCT Filed: Dec. 29, 2017

(86) PCT No.: PCT/IT2017/000296
§ 371 (c)(1),
(2) Date: Jun. 29, 2020

(87) PCT Pub. No.: WO2019/130357
PCT Pub. Date: Jul. 4, 2019

(65) Prior Publication Data
US 2020/0332073 A1    Oct. 22, 2020

(51) Int. Cl.
| C08J 3/075 | (2006.01) |
| A61L 27/20 | (2006.01) |
| A61L 27/52 | (2006.01) |
| C08B 37/08 | (2006.01) |

(52) U.S. Cl.
CPC ............. *C08J 3/075* (2013.01); *A61L 27/20* (2013.01); *A61L 27/52* (2013.01); *C08B 37/0072* (2013.01); *C08J 2305/08* (2013.01)

(58) Field of Classification Search
None
See application file for complete search history.

(56) References Cited

U.S. PATENT DOCUMENTS

| 2002/0141968 A1* | 10/2002 | Zhang ................ A61P 17/02 424/78.38 |
| 2009/0204101 A1* | 8/2009 | Wortzman .......... A61K 8/8152 604/506 |
| 2013/0023658 A1 | 1/2013 | Stroumpoulis et al. |
| 2013/0203696 A1 | 8/2013 | Njikang et al. |
| 2018/0325798 A1* | 11/2018 | Kim .................... A61K 8/96 |

FOREIGN PATENT DOCUMENTS

CN    106 279 726 A    1/2017

OTHER PUBLICATIONS

International Search Report and Written Opinion for PCT/IT2017/000296, dated Aug. 31, 2018.

* cited by examiner

*Primary Examiner* — Dale R Miller
(74) *Attorney, Agent, or Firm* — Marshall, Gerstein & Borun LLP

(57) ABSTRACT

The present invention concerns a method to prepare a filler with a hyaluronic acid, which has improved properties of chemical-physical stability over time and optimal viscosity for cutaneous injection. In particular the method comprises a first step in which the hyaluronic acid is crosslinked, and a subsequent step for the neutralization and hydration of the crosslinked hyaluronic acid.

10 Claims, No Drawings

METHOD TO PREPARE A FILLER WITH A HYALURONIC ACID BASE USING SPECIFIC CROSSLINKING AGENTS

FIELD OF THE INVENTION

Embodiments described here concern a method to prepare a filler with a hyaluronic acid base, which has better properties of chemical and physical stability over time and optimal viscoelasticity to be injected cutaneously.

In particular, the method according to the embodiments described here concerns a method to prepare a filler with a hyaluronic acid base (HA), which comprises a first step in which the hyaluronic acid is crosslinked and a subsequent step to neutralize and hydrate the crosslinked hyaluronic acid.

BACKGROUND OF THE INVENTION

It is known that hyaluronic acid is one of the fundamental components of the connective tissues of man and other mammals. It is a substance widely present in the human body in the epidermal, epithelial and neural tissues.

Hyaluronic acid gives the skin its peculiar properties of resistance and shape retention. A lack of hyaluronic acid causes a weakening of the skin, promoting the formation of wrinkles and imperfections.

The concentration of hyaluronic acid in the tissues of the human body tends to decrease with advancing age, so that its function of tissue repair is weakened. With progressive aging and after repeated exposure to ultra-violet sunrays, the epidermal cells decrease their production of hyaluronic acid and their speed of degradation increases. At the same time, the skin loses collagen, which is another natural substance necessary for maintaining the skin in a young and resilient form. With the passage of time, the loss of hyaluronic acid and collagen in the epidermal tissues causes the formation of folds and wrinkles.

From the chemical point of view, hyaluronic acid (HA) is a polymer compound, definable as a glycosaminoglycan with an un-branched polysaccharide chain, produced by the condensation of thousands of disaccharide units, which are in turn formed by residues of glucuronic acid and M-acetyl-glucosamine.

Thanks to its high solubility in water, the molecule of the salt corresponding to hyaluronic acid, that is, hyaluronate, is able to complex with many molecules of water reaching a high degree of hydration.

Moreover, by using specific crosslinking agents and suitable operating process conditions (temperature, pH, etc.), the extreme length of the hyaluronic acid molecule and its high degree of hydration allow the molecules to organize themselves to form a structure of the lattice type (crosslinked hyaluronic acid), so as to create a molecular scaffold to maintain the shape and tone of the epidermal tissue.

In recent years, various formulations based on hyaluronic acid have been developed for use in esthetic applications in order to fill wrinkles, folds and scars and, in general, to improve the appearance of the face, or to fill the lips.

These formulations are therefore in continuous development from the point of view of industrial research, and are very attractive from the commercial point of view. Hyaluronic acid, being naturally contained in the human body, is a filler that is well tolerated by the epidermal tissue. For this reason, the formulations based on HA are still today considered the best epidermal fillers on the market, because they do not carry the risk of allergic reactions by the skin.

Originally, the first formulations based on hyaluronic acid were prepared in the form of particles or microspheres suspended in a gel. However, these fillers based on gelled microspheres had the disadvantage of poor stability over time, with a tendency to chemical degradation a few months after being injected into the skin. Therefore, frequent re-injections of the filler were required over time, in order to maintain the repair and epidermal growth constant.

In more recent times the advantage has been discovered of subjecting the hyaluronic acid to a suitable crosslinking step by using specific crosslinking agents, and thus fillers based on crosslinked hyaluronic acid are used in esthetic treatments of the face. In this case, the polymer chains of hyaluronic acid are connected to each other to constitute a lattice.

As examples of the most commonly used crosslinking agents, we can cite 1,4-butanediol diglycidyl ether (BDDE), 1,2-ethanediol diglycidyl ether (EDDE), diepoxyoctane and divinyl sulfone. The crosslinking step allows to obtain a hydrogel polymer lattice, which is less soluble in water and more resistant to degradation, so as to require less frequent cutaneous injections than in the case of formulations based on non-crosslinked hyaluronic acid.

However, the use of said crosslinking agents leads to the formation of hydrogels of crosslinked HA which have an excessive level of swelling of the lattice, in the step where the hyaluronic acid is contacted with a chemical neutralizing solution.

Furthermore, an important disadvantage deriving from the crosslinking operating conditions adopted in the state of the art is the formation of fillers based on crosslinked HA with a poor homogeneity of distribution of the chemical-physical parameters (temperature, viscosity, density, etc.) inside the polymer lattice, in the sense that the homogeneity of the structure is interrupted by the unwanted presence of both air microbubbles and lumps of material, that is, narrow zones of thickened material.

This lack of homogeneity of the chemical-physical parameters inside the HA lattice has a negative effect on the chemical-physical stability of the filler prepared, so that its effectiveness over time is unsatisfactory and it is necessary to perform cutaneous re-injections of fillers fairly frequently.

As a consequence of these disadvantages, there is a need to make available in the field of esthetic medicine an innovative method to prepare a filler with a hyaluronic acid base, a method able to increase its chemical-physical stability and duration over time of its repairing action.

There is therefore a need to perfect a method to prepare a filler with a hyaluronic acid base which can overcome the disadvantages of the prior art.

In particular, it is a primary purpose of the present invention to provide a formulation based on hyaluronic acid having better properties of homogeneity/uniformity of the different chemical-physical parameters, so as to increase its stability over time, after it has been used as an esthetic filler.

A second purpose of the method according to the invention is to obtain a filler with a crosslinked HA base having adjustable viscoelasticity in a desired range, by controlling the parameters that define the crosslinking of hyaluronic acid and the subsequent hydration step.

Another purpose of the invention is to improve the efficiency of penetration of a neutralizing solution in the chemical neutralization step that follows the crosslinking of the hyaluronic acid, by means of a selection of innovative operating conditions during the neutralization step.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the present invention or variants to the main inventive idea.

Embodiments described here concern a method to prepare a filler with a hyaluronic acid (HA) base, which comprises a step in which the hyaluronic acid is crosslinked, and a subsequent step for the neutralization and hydration of the crosslinked hyaluronic acid.

The main advantage of the method claimed, which will be described in detail hereafter, is that the operating conditions used allow to obtain formulations with a hyaluronic acid base with innovative and improving characteristics with regard to the homogeneity and uniformity of the different chemical-physical parameters inside it (composition, temperature, viscosity, etc.). Consequently, its chemical-physical stability over time, after cutaneous injection, is considerably increased.

A first aspect of the invention concerns a method to prepare a filler with a hyaluronic acid base comprising the crosslinking of the hyaluronic acid by means of the following steps:
  $A_1$) mixing the following components in a reaction chamber equipped with a mixer: water, hyaluronic acid (HA), a crosslinking agent selected from the class of polyethylene glycols (PEG), a solution of alkali metal hydroxide;
  $A_2$) dividing the mixture thus obtained into a number n of partial portions and transferring said partial portions to a sequence of n containers to subject them to an ultrasound treatment, the number n of partial portions and containers being comprised between 4 and 32, preferably between 8 and 20;
  $A_3$) disposing the n containers comprising these partial portions of mixture in an incubator for a period of time comprised between 4 and 8 hours in order to terminate the crosslinking of hyaluronic acid and promote the formation of a gel of crosslinked hyaluronic acid.

The particular operating conditions adopted during the steps $A_1$), $A_2$), $A_3$) described above, in particular the use of a crosslinking agent selected from the polyethylene glycols and the division of the reaction mixture into n partial portions (step $A_2$), lead to the formation of a lattice of hyaluronic acid HA in a gel form with innovative characteristics with respect to the state of the art techniques. Indeed, this lattice of hyaluronic acid will have a much lower level of swelling during the subsequent neutralization and hydration step.

Embodiments of the present invention also concern defining optimal operating conditions during the chemical neutralization of the hyaluronic acid gel deriving from the crosslinking step described above.

A method to prepare a filler with a hyaluronic acid base is therefore a second aspect of the present invention, and comprises the following steps:
  A) crosslinking the hyaluronic acid by mixing the following components in a reaction chamber: water, hyaluronic acid (HA), a crosslinking agent selected from the class of polyethylene glycols (PEG), a solution of alkali metal hydroxide, the mixing time being comprised between 10 and 40 minutes
  B) a chemical neutralization step of the crosslinked HA gel obtained in step A) comprising:
  $B_1$) preparing a neutralizing solution by mixing the following components: water, hydrochloric acid HCl, a buffer agent, optionally lidocaine or its derivatives;
  $B_2$) dividing the neutralizing solution thus obtained into a number n of partial portions and transferring these partial portions inside the n containers comprising the crosslinked HA gel obtained from step A), where n is a whole number comprised between 4 and 32, preferably between 8 and 20;
  $B_3$) subjecting the n containers to mixing by means of a rotary device, making them rotate around the axis of the rotary device, so as to promote a penetration of the neutralizing solution inside the hyaluronic acid gel, and obtain a filler of crosslinked hyaluronic acid in the form of a hydrogel.

The particular operating conditions adopted during the neutralizing step B), in particular the division (step $B_2$) of the neutralizing solution into a number n of partial portions, and the subsequent gentle rotation to which the n containers are subjected during step $B_3$), allow to improve the penetration efficiency of the neutralizing solution inside the crosslinked HA gel. Consequently, an improved homogeneity and uniformity of chemical-physical parameters inside the filler obtained is obtained.

A third aspect of the present invention also concerns a specific embodiment of the method to prepare a filler with a hyaluronic acid base, which method comprises:
  A) a crosslinking step of the hyaluronic acid comprising the following steps:
  $A_1$) mixing the following components (w/w) in a reaction chamber for a time comprised between 10 and 40 minutes:
    from 25 to 60% in weight of water;
    from 6 to 18% in weight of hyaluronic acid;
    from 25 to 60% in weight of a solution of alkali metal hydroxide;
    from 0.5 to 4% in weight of a crosslinking agent selected from the class of polyethylene glycols;
  $A_2$) dividing the mixture thus obtained into a number n of partial portions and transferring these partial portions to a sequence of n containers to subject them to an ultrasound treatment, the number n of partial portions and containers being comprised between 4 and 32;
  $A_3$) disposing the n containers comprising these partial portions of mixture into an incubator for a time comprised between 4 and 8 hours;
  B) a chemical neutralization step of the crosslinked HA gel obtained in step A) that comprises the following steps:
  $B_1$) preparing a neutralizing solution by mixing the following components (w/w):
    from 78 to 98% in weight of water;
    from 4 to 25% in weight of hydrochloric acid;
    from 0.1 to 1.5% in weight of a buffer agent;
    up to 1.5% in weight of lidocaine or its derivatives;
  $B_2$) dividing the neutralizing solution thus obtained into a number n of partial portions and transferring these partial portions inside the n containers comprising the crosslinked HA gel obtained from step A), where n is a whole number comprised between 4 and 32;
  $B_3$) subjecting the n containers to mixing by means of a rotating device, making them rotate around the axis of the rotating device, so as to promote a penetration of the neutralizing solution inside the hyaluronic acid gel, and obtain a filler of crosslinked hyaluronic acid in the form of a hydrogel.

As well as the advantages correlated to the degree of homogeneity/uniformity of the different chemical-physical parameters (composition, viscosity, etc.) inside it and the consequent temporal increase of its chemical-physical stability, the method according to the embodiments described here allows to suitably adjust the final viscoelasticity of the filler prepared.

Indeed, the control of the crosslinking parameters and the subsequent hydration step of the gel, makes the product stable from the thermodynamic point of view, so that the rheology of the product is also adjusted and maintained under control. The adjustment of the final viscoelasticity of the hyaluronic acid filler allows, in the case of very viscous fillers, to be able to select the type of syringe most suitable for viscous fluids, so that the cutaneous injection can be performed without particular disadvantages linked to high viscosity.

Embodiments of the present invention also concern the use of lidocaine or its derivatives as an anesthetic agent during the chemical neutralization step of the hyaluronic acid gel.

A method to prepare a filler with a hyaluronic acid base is thus another aspect of the invention, which comprises the following steps:

A) crosslinking the hyaluronic acid by mixing the following components in a reaction chamber: water, hyaluronic acid (HA), a solution of alkali metal hydroxide, a crosslinking agent selected from polyethylene glycol diglycidyl ether (PEG DE), polypropylene glycol diglycidyl ether (PPG DE) and polytetramethylene glycol diglycidyl ether, the mixing time being comprised between 10 and 40 minutes;

B) a neutralization step in which the crosslinked HA gel obtained from the crosslinked step A) is contacted with a neutralizing solution comprising the flowing components: water, hydrochloric acid HCl, a buffer agent, lidocaine or its derivatives functioning as an anesthetic agent.

These and other aspects, characteristics and advantages of the present disclosure will be better understood with reference to the following description, drawings and attached claims.

The various aspects and characteristics described in the present description can be applied individually where possible. These individual aspects, for example aspects and characteristics described in the attached dependent claims, can be the object of divisional applications.

It is understood that any aspect or characteristic that is discovered, during the patenting process, to be already known, shall not be claimed and shall be the object of a disclaimer.

DETAILED DESCRIPTION OF SOME EMBODIMENTS

We will now refer in detail to specific embodiments of a method for the preparation of a filler with a hyaluronic acid base (HA), which provides for the steps of crosslinking A) and neutralization B).

Each embodiment is supplied by way of illustration of the invention and shall not be understood as a limitation thereof.

Before describing these embodiments, we must clarify that the phraseology and terminology used here is for the purposes of description only, and cannot be considered as limitative.

All percentages and ratios indicated concern the weight of the total composition (w/w), unless otherwise indicated. All percentage intervals reported here are provided with the provision that the sum with respect to the total composition is 100%, unless otherwise indicated.

All the intervals reported shall be are understood to include the extremes, including those that show an interval "between" two values, unless otherwise indicated.

The present description also includes the intervals that derive from uniting or overlapping two or more intervals described, unless otherwise indicated.

The present description also includes the intervals that can derive from the combination of two or more values taken at different points, unless otherwise indicated.

Embodiments described here concern the preparation of a filler with a hyaluronic acid base which can be used in the cosmetic treatment of the face, in particular to fill wrinkles, folds and scars and, in general, to improve the appearance of the face.

As we said, the crosslinking step A) is carried out by crosslinking agents selected from polyethylene glycols (PEG). In particular, the crosslinking step A) comprises a sequence of at least three steps $A_1$), $A_2$) and $A_3$).

Sub-step $A_1$) involves mixing the following components in a reaction chamber: water, hyaluronic acid (HA), a crosslinking agent selected from the polyethylene glycol class (PEG), a solution of alkali metal hydroxide.

The mixing step $A_1$) of the above components is carried out at a temperature between 10° C. and 30° C., preferably between 15° C. and 25° C., with a mixing time conveniently comprised between 10 and 40 minutes, preferably between 15 and 25 minutes.

With regard to the specific composition of the mixture, the percentage by weight (w/w) of the individual components with respect to the total weight of the mixture can be as follows:

from 25 to 60% water;
from 6 to 18% hyaluronic acid (HA),
from 25 to 60% solution of alkali metal hydroxide,
from 0.5 to 4% of a crosslinking agent selected in the class of polyethylene glycols (PEG).

Preferably but not necessarily, the mixing step $A_1$) of the components indicated can be carried out in two successive steps. In a first step we have the preliminary mixing of water, hyaluronic acid (HA) fed in excess of the water, and a polyethylene glycol with a mixing time maintained between 2 and 6 minutes.

After this period of time, the solution of alkali metal hydroxide, preferably sodium hydroxide NaOH, is added to the mixture obtained, and the mixing of the components is continued for a time comprised between 8 and 25 minutes, preferably between 10 and 20 minutes.

Among the various compounds of the PEG class, it has been noted that, in terms of viscoelastic properties of the HA filler prepared, the best results are obtained by using as crosslinking agents bifunctional PEGs having two epoxy groups at the end of the polymer chain. Among them we can cite, for example, polyethylene glycol diglycidyl ether (PEG DE), polypropylene glycol diglycidyl ether (PPG DE) and polytetramethylene glycol diglycidyl ether.

In the subsequent step $A_2$) the mixture obtained is divided into a number n of partial portions, where n is a whole number comprised between 4 and 32, preferably between 8 and 20. These partial portions of mixture are transferred and fed to a sequence of corresponding n containers to subject them to an ultrasound treatment.

The ultrasound treatment of the n containers is carried out by means of sound waves with a frequency comprised between 40 and 60 kHz.

Moreover, the step $A_2$) of ultrasound treatment is generally carried out at a temperature comprised between 20 and 30° C., for a duration comprised between 5 and 15 minutes.

The ultrasound treatment with the above operating conditions proved to be particularly effective for separating and removing the air microbubbles, which can form during the mixing steps, from the mixture. The air microbubbles represent zones of discontinuity of material inside the formulation obtained, and therefore their presence could compromise the final viscoelastic properties of the filler prepared.

After the ultrasound treatment, the n containers comprising the n partial portions of mixture are disposed inside an incubator to complete the crosslinking reaction between the hyaluronic acid and the polyethylene glycol, that is, performing step $A_3$) of the method in accordance with the present description. Setting the temperature to a constant value comprised between 25° C. and 35° C., the n containers are left inside the incubator for a period of time comprised between 4 and 8 hours, preferably between 5 and 7 hours. After this period of time, the crosslinking of the hyaluronic acid can be defined as terminated, so that a crosslinked hyaluronic acid gel is obtained inside each container.

The crosslinking step A) is carried out in a basic environment due to the presence of a strong base such as sodium hydroxide: therefore, at the end of the crosslinking, hyaluronic acid is obtained in gel form having a pH comprised between 10 and 14.

With these basic characteristics, the gelled formulation obtained absolutely cannot be used for esthetic treatments, as it would cause swelling and burning to the skin, besides being thermodynamically unstable. In fact, at pH values higher than 8, hydrolysis phenomena become likely, which are able to degrade the chemical structure of the hyaluronic acid hydrogel.

The subsequent step B) of neutralizing the HA gel therefore becomes necessary, using a strong acid such as hydrochloric acid.

As explained previously, the neutralization step B) also comprises a sequence of sub-steps $B_1$), $B_2$) and $B_3$).

In step $B_1$) a neutralizing solution is prepared by mixing the following components: water, hydrochloric acid HCl and a buffer agent. The percentage by weight (w/w) of the individual components with respect to the total weight of the neutralizing solution is as follows:

from 78 to 98% water;
from 4 to 25% hydrochloric acid;
from 0.1 to 1.5% buffer agent.

As a buffer agent in step $B_1$) phosphoric acid, potassium phosphate, sodium phosphate can be used. Preferably, phosphoric acid is used.

According to a preferred embodiment, the neutralizing solution can optionally also comprise small quantities of lidocaine or its derivatives, preferably lidocaine hydrochloride is used. This category of compounds are known for their local anesthetic effect, so they have the advantage of reducing itching or burning of the skin during the subcutaneous injection of HA filler. In this case, the percentage by weight (w/w) of lidocaine or its derivatives, with respect to the total weight of the solution, is generally maintained below 1.5%.

According to another preferred embodiment, the neutralizing solution can optionally also comprise small quantities of glycine and/or proline. The presence of these two amino acids has proved advantageous, since they have the dual function of acting as thermodynamic stabilizers of the solution, and of being precursors of the formation of collagen, thus increasing the efficiency of the filler prepared in repairing the tissues.

In this case too, the total percentage by weight (w/w) of proline and/or glycine with respect to the weight of the neutralizing solution is generally maintained below 1%.

In accordance with the present invention, it is convenient to divide (step $B_2$) the neutralizing solution into a number n of partial portions, in the same way as in step $A_2$), n being a whole number comprised between 4 and 32, preferably between 8 and 20.

The partial portions n of neutralizing solution are then transferred into the n containers comprising the crosslinked HA gel obtained from step A).

We then proceed to step $B_3$), which consists in mixing the contents of the n containers using a rotating device: the n containers are put in a gentle rotation around the axis of the rotating device for a duration comprised between 140 and 200 hours.

During the mixing step $B_3$) the temperature is maintained at a value comprised between 20° C. and 30° C., while the speed of rotation of the n containers around the axis of the rotating device is maintained at a rather low value, generally comprised between 40 and 60 rpm.

The particular mixing method described above, inside portions of limited mass, promotes a homogeneous penetration of the neutralizing solution inside the crosslinked hyaluronic acid gel contained in the n containers.

At the same time as the chemical neutralization performed by the action of the hydrochloric acid, an effective penetration of the water molecules inside the meshes of the lattice of gelled hyaluronic acid also takes place: therefore, a considerable hydration of the crosslinked HA gel occurs, with consequent formation of a hydrogel. In practice, the meshes of HA lattice swell due to the penetration of the water molecules, and the degree of swelling of the lattice is indicated by the term "swelling".

It has been proven experimentally that the use of a crosslinking agent selected from polyethylene glycols, as in the method according to the present description, entails a lower degree of swelling of the gelled HA lattice during step B) of neutralization and hydration of the gel.

The hydrogel filler of crosslinked hyaluronic acid obtained from step B) has a complex viscosity that can be comprised between 15 and 45 Pa*s (measured by Kinexus rheometer at 25° C.).

The HA filler in the form of hydrogel obtained in step B) is then subjected to a pH control to verify the effectiveness of the chemical neutralization that has taken place. Consequently, the pH value inside the n containers must be neutral, that is, comprised in a range between 6.5 and 7.5.

Finally, after the pH control test, the hydrogel filler of crosslinked HA prepared by the method described here is suitable to be inserted inside cartridges for syringes for cutaneous injection.

Before being used, the filler storage cartridges have to be subjected to sterilization in autoclave. Autoclave sterilization is performed for 16 minutes at a temperature of 121° C.

To sum up, compared with conventional methods for preparing formulations based on crosslinked hyaluronic acid, the method according to the embodiments described here allows to prepare a crosslinked HA filler which has the following advantages:

1) Innovative and improved characteristics with regard to the homogeneity and uniformity of the different chemical-physical parameters (composition, temperature, viscosity, etc.) inside the filler prepared. It follows that its chemical-physical stability over time, after cutaneous injection, is considerably increased.
2) Adjustment of the final viscoelasticity of the filler prepared by an appropriate selection of the operating conditions during step A) and B) of the method. In this way, the desired rheological properties of the filler are obtained, so that it is possible to select the most appropriate type of syringes for sub-cutaneous injection according to the viscosity of the filler to be injected.
3) The use of a crosslinking agent selected from polyethylene glycols according to the present description involves a lower degree of swelling of the gelled lattice of HA during step B) of neutralization and hydration of the gel. A lower degree of swelling of the lattice is desirable, since it allows to control and limit excess swelling during the sub-cutaneous injection step.
4) The particular operating conditions adopted during the neutralization step B) improve the efficiency of penetration of the neutralizing solution inside the crosslinked HA gel. This aspect also contributes to improving the homogeneity and uniformity of the chemical-physical parameters inside the filler obtained.

It is also obvious that, although method according to the present invention has been described with reference to the embodiments of the crosslinking step A) and neutralization step B) as described above, a person of skill in the art shall certainly be able to achieve many other equivalent forms of a method having the characteristics as set forth in the claims and hence all coming within the field of protection defined thereby.

The invention claimed is:

1. A method to prepare of preparing a filler with a hyaluronic acid base comprising the crosslinking of the hyaluronic acid by means of the following steps:
    A1) mixing the following components in a reaction chamber equipped with a mixer to obtain a mixture: water, hyaluronic acid (HA), a crosslinking agent selected from the class of polyethylene glycols (PEG), and a solution of alkali metal hydroxide;
    A2) dividing the mixture thus obtained into a number n of partial portions and transferring said partial portions to a sequence of n containers to subject the partial portions of mixture to an ultrasound treatment, the number n of partial portions and containers being 4 to 32; and,
    A3) disposing the n containers comprising said partial portions of mixture in an incubator for a period of time of 4 to 8 hours to terminate crosslinking of hyaluronic acid (HA) and promote formation of a gel of crosslinked hyaluronic acid (HA).

2. The method as in claim 1, wherein mixing step A1) is performed at a temperature of 10° C. to 30° C.

3. The method as in claim 1, wherein in step A1) a mixing time is 10 minutes to 40 minutes.

4. The method as in claim 1, wherein in step A1) a percentage in weight of the individual components with respect to the total weight of the mixture (w/w) is as follows:
    from 25% to 60% water;
    from 6% to 18% hyaluronic acid;
    from 25% to 60% solution of alkali metal hydroxide; and
    from 0.5% to 4% crosslinking agent selected from the class of polyethylene glycols.

5. The method as in claim 1, wherein mixing step A1) comprises two sub-steps in sequence:
    preliminarily mixing water, hyaluronic acid (HA) fed in excess with respect to the water, and crosslinking agent selected from the class of PEGs, with a maintained mixing time of 2 minutes to 6 minutes to obtain a sub-mixture; and,
    subsequently adding the sub-mixture to the solution of alkali metal hydroxide to form the mixture of claim 1 and continue mixing the mixture of claim 1 for a time of 8 minutes to 25 minutes.

6. The method as in claim 1, wherein the crosslinking agent is selected from bifunctional PEGs having two epoxy groups at an end of a polymer chain.

7. The method as in claim 6, wherein said bifunctional PEGs are selected from polyethylene glycol diglycidyl ether (PEG DE), polypropylene glycol diglycidyl ether (PPG DE), and polytetramethylene glycol diglycidyl ether.

8. The method as in claim 1, wherein in step A2) said number n is 8 to 20.

9. The method as in claim 1, wherein the ultrasound treatment step in step A2) is performed by acoustic waves with a frequency of 40 kHz to 60 kHz.

10. The method as in claim 1, wherein a duration of the ultrasound treatment in step A2) is 5 minutes to 15 minutes.

* * * * *